(12) United States Patent
Barcikowski et al.

(10) Patent No.: US 10,035,112 B2
(45) Date of Patent: Jul. 31, 2018

(54) METHOD FOR MANUFACTURE OF PURE, CARBON FREE NANOPARTICLES

(71) Applicant: Universitaet Duisburg Essen, Essen (DE)

(72) Inventors: Stephan Barcikowski, Essen (DE); Marcus Lau, Essen (DE)

(73) Assignee: Universitaet Duisburg Essen, Essen (DE)

( * ) Notice: Subject to any disclaimer, the term of this patent is extended or adjusted under 35 U.S.C. 154(b) by 1032 days.

(21) Appl. No.: 14/089,393

(22) Filed: Nov. 25, 2013

(65) Prior Publication Data
US 2014/0171523 A1 Jun. 19, 2014

(30) Foreign Application Priority Data

Nov. 23, 2012 (EP) ..................................... 12194129

(51) Int. Cl.
*B01F 3/12* (2006.01)
*B22F 1/00* (2006.01)
(Continued)

(52) U.S. Cl.
CPC .......... *B01F 3/1235* (2013.01); *B22F 1/0018* (2013.01); *B22F 1/0022* (2013.01);
(Continued)

(58) Field of Classification Search
CPC .. B01F 3/1235; B23K 26/0066; B22F 1/0018; B22F 1/0022; B22F 9/04;
(Continued)

(56) References Cited

U.S. PATENT DOCUMENTS 9,603,870 B2 * 3/2017 Mortenson ............ B22F 1/0022
2009/0229968 A1 * 9/2009 Takeda ..................... A62D 3/10
204/157.15
(Continued)

FOREIGN PATENT DOCUMENTS

WO WO 2010/007117 1/2010
WO WO 2010/087869 8/2010
WO WO 2012/080458 6/2012

OTHER PUBLICATIONS

Mafune' et al., Formation of Gold Nanoparticles by Laser Ablation in Aqueous Solution of Surfactant, J. Phys. Chem. B 2001, 105, 5114-5120.*
(Continued)

*Primary Examiner* — Daniel S Metzmaier
(74) *Attorney, Agent, or Firm* — Greer, Burns & Crain, Ltd.; Steven P. Fallon

(57) ABSTRACT

The invention provides a process for the production of nanoparticles as well as a device that is disposed for the production of the nanoparticles. The process is especially characterized in that the nanoparticles are pure, especially free from organic carbon compounds, preferably carbon-free, and are obtained continuously. The nanoparticles which are obtainable by the process of the invention are characterized in that they are present without an organic ligand in suspension and are especially preferred stable as a suspension against agglomeration, wherein the medium having the particles suspended therein is free from organic carbon compounds, especially carbon-free.

30 Claims, 11 Drawing Sheets

Figure 1:
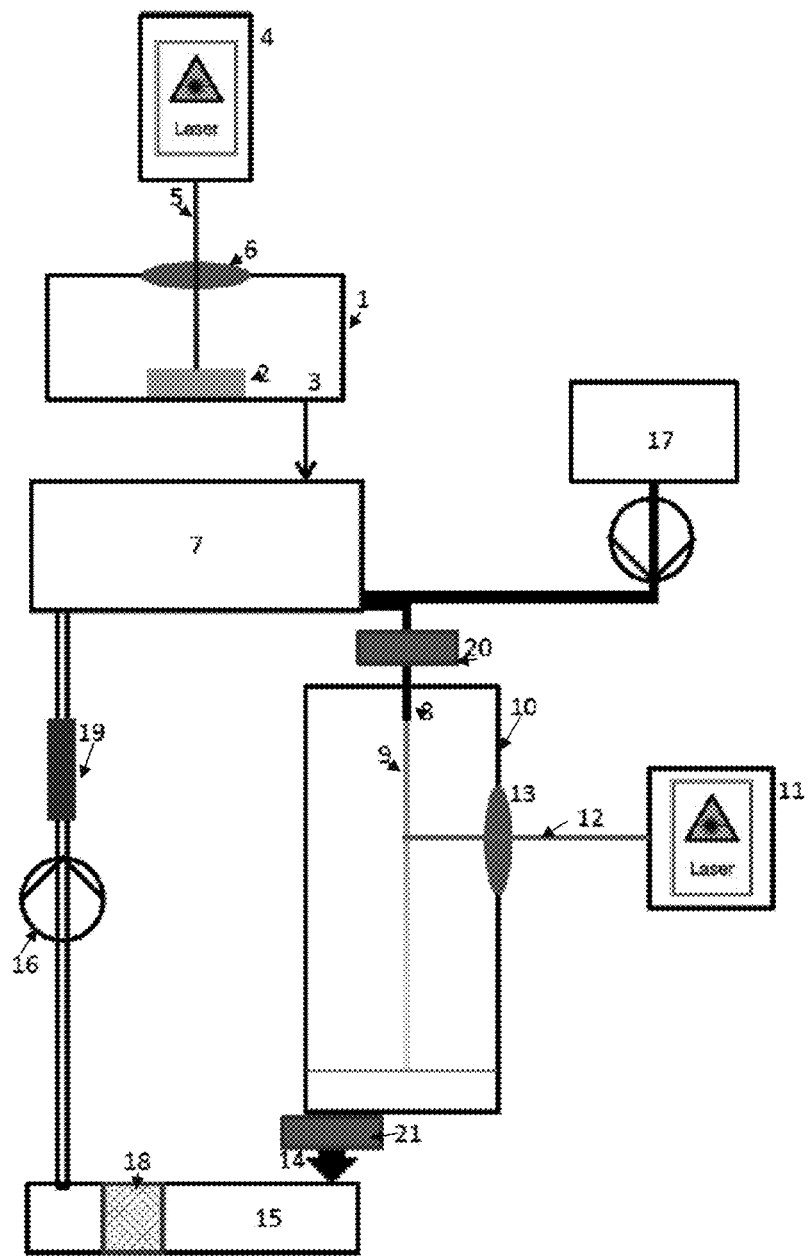

(51) Int. Cl.
| | |
|---|---|
| *B22F 9/04* | (2006.01) |
| *B23K 26/00* | (2014.01) |
| *B82Y 30/00* | (2011.01) |
| *A61K 33/24* | (2006.01) |
| *A61K 49/00* | (2006.01) |
| *G01N 33/58* | (2006.01) |
| *G01N 33/553* | (2006.01) |

(52) U.S. Cl.
CPC ............ *B22F 9/04* (2013.01); *B23K 26/0066* (2013.01); *B82Y 30/00* (2013.01); *A61K 33/24* (2013.01); *A61K 49/0065* (2013.01); *G01N 33/553* (2013.01); *G01N 33/587* (2013.01)

(58) Field of Classification Search
CPC .. G01N 33/553; G01N 33/587; G01N 33/588; G01N 21/554; A61K 33/24; A61K 49/0067
USPC .................................... 516/97; 977/888, 889
See application file for complete search history.

(56) References Cited

U.S. PATENT DOCUMENTS

| | | | | |
|---|---|---|---|---|
| 2009/0317289 | A1* | 12/2009 | Ito .......................... | B01J 19/121 420/461 |
| 2011/0189695 | A1 | 8/2011 | Barcikowski et al. | |
| 2011/0303050 | A1* | 12/2011 | Gondal .................. | B82Y 30/00 75/347 |
| 2013/0178357 | A1* | 7/2013 | Adzic ................. | H01M 4/9041 502/5 |
| 2014/0038815 | A1* | 2/2014 | Koga ....................... | B01J 23/56 502/331 |
| 2014/0065718 | A1* | 3/2014 | Im ............................ | C01G 7/00 436/135 |
| 2014/0294963 | A1* | 10/2014 | Dorfman .................. | A61K 9/14 424/489 |

OTHER PUBLICATIONS

Muto et al., Estimation of Surface Oxide on Surfactant-Free Gold Nanoparticles Laser-Ablated in Water, J. Phys. Chem. C 2007, 111, 17221-17226.*
Lopez-Sanchez, Jose A. et al., "Facile removal of stabilizer-ligands from supported gold nanoparticles", *Nature Chemistry*, 3, Jun. 5, 2011; pp. 551-556.
Nichols, William T., et al., "Laser ablation of a platinum target in water. I. Ablation mechanisms", *Journal of Applied Physics*, 100 (11), Dec. 2006, pp. 114911-1-114911-6.
Sylvestre, Jean-Phillipe, et al., "Surface Chemistry of Gold Nanoparticles Produced by Laser Ablation in Aqueous Media", *J. Phys. Chem B*, 108, Oct. 6, 2004, pp. 16864-16869.
Wagener, Philipp, et al., "How Citrate Ligands Affect Nanoparticle Adsorption to Microparticle Supports", *Lagumuir*, Mar. 14, 2012, 28 (14), pp. 6132-6140.
Werner, Daniel, et al., "In-Situ Spectroscopic Measurements of Laser Ablation-Induced Splitting and Agglomeration of Metal Nanoparticles in Solution", *J. Phys. Chem. C*, vol. 112, No. 43, 2008, pp. 16801-16808.
Bueno-Alejo, Carlos, et al., "Ultraclean Derivatized Monodisperse Gold Nanoparticles through Laser Drop Ablation Customization of Polymorph Gold Nanostructures", Langmuir, vol. 28, (2012), pp. 8183-8189.
Lau, Marcus, et al., "Ligand-free gold atom clusters adsorbed on graphene nano sheets generated by oxidative laser fragmentation in water", Chemical Physics Letters, vols. 610-611, (2014), pp. 256-260.

* cited by examiner

METHOD FOR MANUFACTURE OF PURE, CARBON FREE NANOPARTICLES

The present invention relates to a process for the production of small nanoparticles and atomic clusters, preferably of gold, which especially have a diameter of small than 5 nm, preferably smaller than 3 nm and are preferably free from organic carbon compounds, especially free from hydrocarbons, e.g. as the only carbon compound have $CO_2$, especially dissolved in water, e.g. as carbonate anions, and which are especially preferred carbon-free, e.g. in an aqueous composition. Further, the invention relates to the nanoparticles obtainable by the process, which are present especially in suspension and are stable against agglomeration, wherein the suspension is free from organic carbon compounds, especially hydrocarbon-free, e.g. having as the only carbon compound $CO_2$, especially dissolved in water, e.g. as carbonate anions and which is especially preferred carbon-free. Insofar, the nanoparticles produced according to the invention are pure. In suspension, which especially is an aqueous suspension, the nanoparticles can be present in the form of clusters, which preferably are complete orbital clusters, especially of a defined number of atems, e.g. Au-clusters of 55 atoms. Subsequent to their production, the nanoparticles can optionally be adsorbed to one another.

Further, the invention relates to a device, which is adapted to the production process for nanoparticles.

Further, the invention relates to compounds and coatings of the nanoparticles obtained by the process, especially to organic molecules connected to the nanoparticles, especially biologically active compounds, as well as inorganic carriers coated with the nanoparticles, electrodes and optical components, especially optical elements having a coating of the nanoparticles. Such compounds are e.g. obtained by contacting the nanoparticles, which are at least free from organic carbon compounds, with an organic molecule. The nanoparticles preferably consist of a noble metal, e.g. of gold and/or a platinum metal, e.g. platinum.

STATE OF THE ART

WO 2012/080458 A1 describes a process for producing metal nanoparticles by laserablation, which subsequently are mixed with water insoluble microparticles in suspension in order to adsorb the nanoparticles to the microparticles. In the process, the degree of oxidation of the nanoparticles can be influenced by utilization of an organic solvent, especially of acetone, methanol or isopropanol, or by utilization of ligands, e.g. by sodium citrate.

WO 2010/087869 A1 describes the production of nanoparticles by ultrashort pulsed laserablation in liquids, which is characterized in that the liquid, especially water, shall not contain chemical stabilizers, wherein the stability of the suspension of the nanoparticles can be increased by agitation of the liquid.

WO 2010/007117 describes a process for the production of conjugates of metal nanoparticles with an organic constituent by irradiating a metal body with a laser beam, wherein the carrier fluid, which is admixed with a precursor compound of the organic constituent, surrounds the metal body and is agitated.

Lopez-Sanchez et al, Nature Chemistry 1-6 (2011) describe the production of metal nanoparticles in a reducing medium having polyvinyl alcohol (PVA) as a stabilizer which was at least partially removed from supported nanoparticles by warming up to 400° C. or by washing with hot water.

Werner et al, J. Phys. Chem. C 16801-16808 (2008) describe the production of suspended gold nanoparticles by laser irradiation of gold flakes having a thickness of 0.1-0.2 µm to nanoparticles of smaller than 3 nm only in presence of organic solvent, which disintegrates under laser irradiation. Upon laser irradiation of the gold flakes in water a previously generated $O_2$-content of the water leads to fast agglomeration and precipitation of nanoparticles generated, while the previous gassing with argon or a content of citrate prevents this. Non-plasmon resonant particles could only be generated by means of laser irradiation from gold flakes upon addition of the organic stabilizer dodecanthiol.

Sylvestre et al, J. Phys. Chem. B 16864-16869 (2004) describe that the laser irradiation of a gold rod in pure water results in particles of 1-250 nm having a mean size of 40 nm, and in NaCl or KCl or propylamine, each 10 mM, or in NaOH, the size distribution decreases and the mean particle size goes down to 5.5-8 nm.

Nichols et al, J. Appl. Phys. 114911 (2006) describe the progress of the production of nanoparticles by laser irradiation of a platinum plate in water, especially the formation of craters on the platinum plate, and its dependence on the laser irradiation.

OBJECT OF THE INVENTION

The object posed to the invention is to provide an alternative process for the production of nanoparticles, which can be clusters, which preferably form a stable suspension in medium without an organic carbon component, e.g. in a carbon-free medium like water. A further object lies in the provision of nanoparticles, which can be clusters, especially of gold, which have a homogenous particle size distribution, as well as compounds containing the nanoparticles.

GENERAL DESCRIPTION OF THE INVENTION

The invention achieves the object by the features of the claims and provides a process for the production of nanoparticles, the special nanoparticles produced by the process, as well as a device which is disposed for the production of the nanoparticles. The process is especially characterized in that the nanoparticles are pure, especially free from organic carbon compounds, preferably carbon-free, and are obtained continuously. The process can entirely or partially be performed continuously and is therefore scalable in a simple manner. The nanoparticles which are obtainable by the process according to the invention are characterized in that they are present in suspension without an organic ligand, especially without an organic compound as stabilizer, and especially as a suspension are stable against agglomeration, wherein the medium with the particles suspended therein is free from organic carbon compounds, especially preferred carbon-free. Generally, under the nanoparticles according to the invention there are summarized clusters of metal atoms, especially complete orbital clusters.

The process for the production of nanoparticles provides to generate first particles from a metal-containing body using a first laser irradiation, which is especially pulsed, preferably a short-pulsed irradiation, wherein the metal-containing body is arranged in an aqueous medium. The metal-containing body can especially be a metal body (oxidation stage 0), optionally in the form of a wire or a powder or micro powder (grain size e.g. from 1 µm to 500 µm), which can be suspended in the medium. As the metal, especially a metal of the platinum group, subsequently also termed platinum metal, e.g. platinum, preferably gold, can be contained; preferably the metal containing body consists of gold, preferably having a purity of more than 99.9%, optionally of an alloy of two or more metals of the platinum group, e.g. AuPt.

The first laser irradiation preferably is a short-pulse irradiation having a high puls energy, especially having a puls energy of 1 to 100 mJ, especially having repetition rates of from 10 Hz to 500 kHz, especially 0.1 to 10 kHz, e.g. having a pulse duration of 100 ns, preferably of maximally 10 ns, more preferably maximally 10 ps, at a wavelength of larger than 330 nm and maximally 1500 nm, especially in the range of from 532 to 1064 nm, preferably 1064 nm. The duration of the irradiation of the metal body preferably amounts to ca. 5 to 10 min, e.g. 10 min for 100 mL medium each, at a pulse energy of ca. 80 mJ at 10 ns pulse duration or ca. 100 µJ at 10 ps puls duration.

Generally preferred, the medium is agitated during irradiation of the metal containing body with the first laser irradiation, e.g. by stirring or streaming about of the metal containing body with the medium. Alternatively or additionally, the first laser irradiation is moved relatively to the metal containing body, e.g. by moving the laser beam or by moving the metal body. According to the invention, the medium preferably contains or consists of water, which is preferably free from organic carbon compounds, especially containing as the single carbon compound $CO_2$, and more preferably is carbon-free, optionally having a content of at least one inorganic oxidizing agent. The inorganic oxidizing agent can e.g. be selected from $H_2O_2$, ozone, hypohalogenic and halogenic oxidizing agents and all non-carbon containing oxidatively acting compounds, e.g. derivatives of oxygen—hydrogen compounds, nitrogen oxides, antimonic acid, arsenious acid, arsenic acid, boric acid, chlorous acid, bromous acid, chloric acid, chromic acid, cyanic acid, dichromic acid, disulphuric acid, hypochlorous acid, hypobromous acid, hypoiodous acid, iodous acid, iodic acid, isocyanic acid, carbonic acid, metasilicilic acid, molybdic acid, orthodisilicilic acid, orthosilicilic acid, perbromic acid, perchloric acid, periodic acid (orthoperiodic acid), peroxodisulphuric acid, peroxonitric acid, nitric acid, nitrous acid, sulphuric acid, sulphurous acid, telluric acid, thiosulphuric acid, tungstic acid and its salts, hypofluorous acid, hypofluorites, oxyacids of chlorine, hypochlorites, chlorites, chlorates, perchlorates, oxyacids of bromine, hypobromites, bromous acid, bromites, bromic acid, bromates, perbromic acid, perbromates, oxyacids of iodine, hypoiodites, iodites, iodic acid, iodates, orthoperiodic acid, periodates, metaperiodic acid and mixtures of these.

Preferably, the oxidizing agents in the aqueous medium has a redox potential higher than that of the oxidized forms of gold or that of a metal of the platinum group which are generated by the laser irradiation, especially higher than the redox potential of $Au^+$ and/or $Au^{3+}$ in the medium. Preferably, the oxidizing agent in the aqueous medium has a redox potential higher by at least 0.05 V, preferably at least 0.09 V, or preferably at least 0.15 V or at least 0.2 V, more preferably at least 0.3 to 0.38 V than an oxidized form of gold or of a platinum metal, respectively. Presently it is assumed that the effect of the inorganic oxidizing agent is based on maintaining or preserving the nanoparticles generated by the (second) laser irradiation which is directed onto the first particles. Accordingly, what matters for this effect in a preferred embodiment is that the inorganic oxidizing agent has a higher redox potential than that present on the oxidized form of the gold and of the metal of the platinum group, respectively, in the size of the nanoparticles, especially in a size of 1 to 5 nm. The dependency of the redox potential of the oxidized form of gold and of the metal of the platinum group, respectively, on their particle size is generally known. Therein, the redox potential of the oxidized form of gold and of the metal of the platinum group, respectively, which optionally is a higher or lower oxidation stage thereof, at the size of the nanoparticles can be smaller than the redox potential of larger particles of gold and of the metal of the platinum group, respectively, in their oxidized form.

Further preferred, the inorganic oxidizing agent, especially when it is a gas present in the aqueous medium, e.g. a dissipated or dissolved gas, has a redox potential which is higher at least by the amount of the overpotential of the nanoparticles than the redox potential of the oxidized form of gold and of the metal of the platinum group, respectively, which optionally are present in the size of the nanoparticles.

The redox potential of the oxidized form of gold and of the metal of the platinum group, respectively, in the size of the nanoparticles in the aqueous medium and/or the overpotential of these nanoparticles can be predetermined, e.g. for nanoparticles, which are generated by the process of the invention using $H_2O_2$ in water, especially as described in Example 1.

As the redox potential of oxidized forms of gold and of the metal of the platinum group, respectively, can depend on the pH of the aqueous medium, the aqueous medium optionally contains a buffering substance which is free from organic carbon, e.g. carbonate, phosphate, optionally in combination with a further acid or base, which adjusts the pH of the aqueous medium to a value at which the redox potential of the oxidizing agent is above that of the oxidized forms of the gold and of the metal of the platinum group, respectively.

Redox potentials under standard conditions

| Designation | formula | redox potential (at pH 0 against hydrogen electrode) | pH 7 | pH 14 |
| --- | --- | --- | --- | --- |
| water | $H_2O$ | +1.23 V | +0.82 V | −0.828 V |
| oxygen | $O_2$ | +1.23 V | +0.82 V | |
| gold | $Au^+$ | +1.69 V | | +1 V |
| gold | $Au^{3+}$ | +1.5 V | | +0.535 V |
| hydrogen peroxide | $H_2O_2$ | +1.78 V | | |
| ozone | $O_3$ | +2.07 V | | |
| atomic oxygen | O | +2.42 V | | |

Further preferred, the aqueous medium contains the oxidizing agent in a molar concentration of at least the 1000-fold, preferably of at least the 2000-fold, more preferably at least the 10,000-fold, further preferred to the at least 100,000-fold or at least 200,000-fold of the calculated concentration of nanoparticles having a size of 2 nm. The mass concentration of nanoparticles of a size of 2 nm results from the mass concentration of the first particles utilized in the process in mg/L.

Alternatively, first particles can be generated by removing organic compounds from a preparation of first particles, wherein this preparation is obtainable e.g. by a sol-gel-process and contains organic compounds as stabilizer, e.g. PVA and/or organic solvent. For example, first particles can be generated by the process described by Lopez-Sanchez et al, Nature Chemistry 1-6 (2011). Preferably, organic compounds in this preparation are bound to the first particles. For removal of organic compounds, this preparation can be heated, e.g. to 200° C. up to 400° C. or above, preferably up to a temperature below the melting temperature of the first particles and/or can be washed using a medium which does not contain organic carbon compounds, which is especially carbon-free, e.g. at least 3-times, especially in the aqueous medium, and/or can be oxidized, e.g. by contacting with an oxidizing agent which disintegrates organic components to $CO_2$ and non-carbon containing products. In the alternative to contacting with oxidizing agent for removal of organic carbon compounds, the preparation can be exposed to a laser irradiation.

Organic carbon compounds, e.g. citrate, polyvinyl pyrrolidon (PVP), polyvinyl alcohol (PVA), polyethylene glycol (PEG), tannic acid and/or inorganic ions, e.g. alkaline, earth alkaline ions, halogen ions and further inorganic anions, e.g. phosphate, sulphate, which are contained in a preparation of first particles, can e.g. be remainders from synthesis or act as stabilizers of the first particles.

The first particles, especially when they are generated by a first laser irradiation to a metal in water preferably have e.g. for at least 90%, more preferred for at least 95% of particles a size of at least 10 nm to maximally 250 nm, more preferred up to maximally 50 nm, still preferred from 10 to 35 nm, e.g. with a medium size of ca. 18 to 22 nm.

The process according to the invention provides for first particles, which were generated by applying the first laser irradiation onto the metal containing body or by applying a first laser irradiation onto a preparation of first particles containing organic compounds as stabiliser, which particles are contained in the medium be irradiated with a pulsed laser irradiation, which is also designated as second laser irradiation, or as a second pulsed laser irradiation, for producing the nanoparticles according to the invention. Therein, preferably a flow of the medium is generated having the first particles suspended therein which medium is free from organic carbon compounds, especially containing $CO_2$ as the sole carbon compound, and more preferred is carbon-free, wherein the medium contains an inorganic oxidizing agent, and this flow is irradiated with the second pulsed laser irradiation. Preferably, the flow of the medium is a free flow, for example a flow which is without contact to a solid surface at least in that section which is irradiated by the second pulsed laser irradiation. Specifically, the flow of the medium at least in that section irradiated by the second pulsed laser irradiation is not conducted in a tube, e.g. in the form of a continuous or drop-shaped fluid flow in a gas-filled space. The flow of the medium having the first particles suspended therein in an advantageous manner allows the irradiation with high fluence.

In the alternative, the first particles that are contained in the medium having an inorganic oxidizing agent can be irradiated with the second laser irradiation, while the medium is motionless in a container. With this process control it is preferred that the second laser irradiation is moved relative to the medium, especially by moving the medium, e.g. by means of a stirrer or by circulating.

Generally, the first particles can be produced by an alternative process that replaces their production by means of irradiating a metal containing body with a first laser irradiation. For the purposes of the invention, also in this embodiment the laser irradiation which is directed onto the first particles can be designated as second laser irradiation. Especially in alternative embodiments of the process the inorganic oxidizing agent can be added to the medium which contains the first particles prior to or following the production of first particles. Such an alternative process for producing first particles can e.g. contain the steps of wire erosion, wherein e.g. a metal containing body, especially in wire form, e.g. a wire of gold and/or of a platinum metal is subjected to electric voltage in water.

The inorganic oxidizing agent can be pre-arranged in the medium, in which the metal containing body is arranged during the irradiation with first laser irradiation and/or can be added continuously or batch-wise during the irradiation with first laser irradiation. In the alternative or additionally, the inorganic oxidizing agent can be added to the medium continuously or batch-wise prior to irradiation with the second laser irradiation.

Optionally, the medium can contain inorganic ions, e.g. alkaline ions, earthalkaline ions, halogenic ions and/or inorganic ions, e.g. phosphate, sulphate; preferably, the medium consists of water and at least one inorganic oxidizing agent and is free from inorganic ions.

In embodiments, in which first particles comprise inorganic ions and/or organic compounds, e.g. as described in relation to preparations of first particles, inorganic oxidizing agent is preferably added to the medium in a quantity sufficient for oxidation of the organic compounds in addition to an oxidative environment, wherein the additional amount is sufficient e.g. at least for oxidation to $CO_2$ especially of organic compounds which are present in admixture with first particles.

Optionally, the pH value of the medium is adjusted prior to irradiation with first laser irradiation and/or prior to irradiation with second laser irradiation to a value of 3 to 6.5. In the alternative, the first particles can have organic ligands, e.g. can be kept in suspension by organic stabilizing compounds. Such first particles having organic ligands or stabilizing compounds in one embodiment of the process can be irradiated with laser irradiation which in combination with the inorganic oxidizing agent generates nanoparticles which are free from organic ligands. Presently, this is attributed on the one hand to the reduction of the size of first particles to nanoparticles during the process, resulting in an extreme dilution of the organic ligands or stabilizing agents during the process, which essentially results in the absence of organic ligands or stabilizing agents from the nanoparticles, and on the other hand to the destruction of organic ligands or stabilizing agents by the laser irradiation, e.g. to their oxidation to inorganic carbon compounds, especially to CO and $CO_2$ in the aqueous medium.

Preferably, the second laser irradiation is focused on the flow of the medium having the first particles suspended therein, wherein preferably the diameter of the flow of the medium having the first particles suspended therein at maximum is so large as the focus of the second pulsed laser irradiation. Preferably, the wavelength of the second laser irradiation is within the range of the extinction maximum of the first particles suspended in the medium, e.g. in the green range, especially at 510 to 540 nm.

The second pulsed laser irradiation can have the characteristics as described with reference to the first laser irradiation, especially at a repetition rate of at least 10 Hz, more preferred of at least 100 Hz, more preferred of the least 1000 Hz, especially for pulse durations of from 1 to 100 ns, at 1 to 500 kHz for pulse durations of 0.5 to 100 ps, preferably 1 to 20 ps.

One reason for the medium having the first particles suspended therein being conducted preferably in a free flow at least in that section in which it is irradiated by the second pulsed laser irradiation is the avoidance of interactions of the laser irradiation and/or of the particles generated with a wall material. Further, in these embodiments high laser fluences, e.g. at a laser fluence of 0.1 to 25 $J/cm^2$, preferably >1 $J/cm^2$ are possible, without an ultrasound wave, cavitation bubble, shock wave, laser absorption or thermal effects occurring burdening the wall material contacting the flow, especially a capillary. This process and the device utilized therefore allow an intense irradiation of the particles and especially the production of nanoparticles having a narrow particle size distribution which is advantageous for the stability of the nanoparticles in suspension.

The medium in which the metal containing body is arranged during the application of the first pulsed laser irradiation can differ from the medium from which a flow is generated, wherein in this medium the first particles are suspended. For example, the medium in which the metal containing body is arranged during irradiation with the first pulsed laser irradiation can be an aqueous medium, it especially can be free from an inorganic oxidizing agent, especially consist of pure water, while the medium from which the flow is generated of which at least a section is irradiated with the second pulsed laser irradiation contains the inorganic oxidizing agent, and can especially consist of water and at least one inorganic oxidizing agent. Preferably, the pH value and the content of dissolved gas of the medium in which the metal containing body is arranged during the application of the first pulsed laser irradiation is set, e.g. by addition of inorganic acid and base, respectively, e.g. by gassing or outgassing.

Preferably the flow in that section in which it is irradiated by the second laser irradiation has a diameter of at maximum 3 mm, especially of 1 to 3 mm, e.g. of 1.2 mm, wherein e.g. the second laser beam has a raw beam diameter of at maximum 8 mm, preferably at maximum 6 mm. Further preferred, the flow is directed vertically to the ground, e.g. a free vertically falling flow of the medium having the first particles suspended therein. Preferably, the second laser beam is directed perpendicularly to the flow of this medium.

Preferably, the flow is generated by the medium having the first particles suspended therein exiting through a nozzle, the longitudinal axis of which is preferably arranged vertically. The nozzle is preferably provided continuously with the medium having the first particles suspended therein, e.g. from a feeding reservoir, preferably immediately subsequent to the application of the first pulsed laser irradiation onto the first metal containing body, such that the medium having the first particles suspended therein is used within 60 min, preferably within 10 min, more preferred within 1 min for generating the flow, for example by admission to a nozzle.

In the alternative to a free flow, the medium containing the first particles can be contained in a container while being irradiated with the pulsed laser irradiation, without or with movement of the liquid. Such a container can be closed or open and contain the medium having the first particles, or can be flowed through by the medium having the first particles. A container can e.g. be a flow-through chamber or a tube, respectively, wherein the pulsed laser irradiates through a volume section, wherein the laser is especially arranged to irradiate through each volume element of the medium having the first particles at least or exactly one time.

Further preferred, inorganic oxidizing agent is added to the medium following irradiation with the first laser beam, e.g. added in dependence on the concentration and/or size of nanoparticles generated in a controlled manner. The inorganic oxidizing agents added subsequently can be that which is contained by the medium prior to irradiation with the second laser beam, or another inorganic oxidizing agents.

The nanoparticles generated by the process preferably have a maximum size of approximately 5 nm, especially having a mean size of 2 to 3 nm, especially of 2.5 nm. Preferably, at least 50%, more preferred at least 75%, especially preferred at least 90% of nanoparticles have such a mean size. Upon presence of these nanoparticles in a medium in suspension, which consists of the medium and these nanoparticles, and therefore contains especially no further particles, e.g. no first particles, the nanoparticles produced according to the invention preferably are not surface plasmon resonant, e.g. nanoparticles of gold produced according to the invention are not surface plasmon resonant upon irradiation with a wavelength of 520 nm. Nanoparticles which are clusters can be complete orbital clusters such as $M_{55}$, $M_{309}$, $M_{561}$, especially $Au_{55}$ or $Pt_{309}$.

It was found that irradiating the flow of medium, to which an inorganic oxidizing agent is added and having the first particles suspended therein by a pulsed laser irradiation which for the purposes of the invention is also referred to as the second pulsed laser irradiation generates nanoparticles of this size.

Surprisingly it has shown that the presence of an inorganic oxidizing agent in the medium which contains first particles generated by laser irradiation of a metal containing body results in the stability for generation of a stable composition or to a stable distribution of nanoparticles in the medium, respectively, by irradiation of the flow with a second pulsed laser irradiation. Correspondingly, it is a specific advantage of the process according to the invention and of the nanoparticles obtainable thereby that the composition and the medium, respectively, in which the nanoparticles are contained, does not need to contain a stabilizing agent, especially no organic compounds. The stability of the suspension of nanoparticles against aggregation is presently attributed to the at least partial superficial, preferably complete superficial oxidation of the nanoparticles and to the nanoparticles being stabilized electrostatically in suspension, respectively.

Due to be generated nanoparticles being stable without organic carbon compound, and carbon free in the medium, they can react with an added substance without separation of a carbon compound, and can e.g. form a complex compound, chemisorb or form a coating, which especially consists of the nanoparticles, and is especially free from carbon. Such complex compounds of nanoparticles or of coatings of nanoparticles which are free from organic carbon compounds, especially carbon-free coatings of nanoparticles have a significant catalytic activity. For coatings of the nanoparticles, the catalytic activity is attributed to the large surface area of the nanoparticles and/or to the interaction of the nanoparticles with the substrate and to the surface of the nanoparticles not being covered by carbon compounds.

Correspondingly, the process preferably contains the step to subsequently contact the nanoparticles in the medium with a substance, which for example is a biological molecule, especially selected from nucleic acids, for example an oligonucleotide, a protein, peptide, glycoside and/or a lipid. Preferably, the protein is a specific binding molecule, e.g. an antibody which is contacted with the nanoparticles and forms a compound with it. The biological molecule preferably comprises a thiol group or a disulfide group. Alternatively or additionally, the substance can be a carrier, especially an inorganic carrier, such that the nanoparticles can be deposited on this carrier and coat the carrier. To this effect it is preferred that the nanoparticles are deposited electrophoretically on the inorganic carrier in order to form a superficial coating. Such an inorganic carrier especially is a catalyst carrier, for example a titanium oxide, such that e.g. the nanoparticles form a catalytically active coating, or the inorganic carrier can be an electrode on which the deposited nanoparticles form a coating. An electrode having a coating of the nanoparticles is especially suitable for use as an electrophysiological electrode. In these embodiments it is an advantage of the nanoparticles according to the invention that these upon irradiation with an excitation wavelength generate a fluorescence signal which is influenced by a substance bound to the nanoparticles and which is specific for the bound substance, respectively.

Preferably, the nanoparticles are coupled directly to the carrier, e.g. by chemisorption or physisorption. A direct electrochemical coupling of the nanoparticles to a substance, which especially is a biological molecule, or to a carrier, allows an orbital coupling, resulting in electro-chemiluminescence or fluorescence. The absence of organic carbon compounds, preferably of carbon, from the nanoparticles utilized comprises no further organic carbon compounds to the substance contacted or bound to the nanoparticles, and a coating of the nanoparticles contains no organic carbon compounds which influence the interaction of the nanoparticles with the substance and the carrier, respectively, or influences the reaction of the substance bound to the nanoparticles or of the coating on the carrier. Therefore, compounds having characteristics, e.g. reactive or binding characteristics, which are not impaired by organic carbon compounds can be generated of substances or coatings on carriers from the nanoparticles according to the invention.

Furthermore, the substance or the carrier, respectively, can be an optically active carrier, for example an optically transparent carrier, especially of glass or synthetic material, such that the deposition of the nanoparticles produced according to the invention on the carrier results in an optically active coating. In this embodiment, the process results in the production of an optical element, as the coating of the nanoparticles produced according to the invention is an optically active coating on the carrier, which coating e.g. under incident light of a predetermined wavelength quickly reduces the transmittance of the coating therefore that of the optical element when reaching or exceeding a certain irradiated fluence intensity, especially reducing by at least 50%, more preferred by at least 90%, more preferred by at least 99%. Such an optical element can e.g. serve as an optical switch, especially for laser irradiation, which can optionally be pulsed, especially at a wavelength of 350-1065 nm, or for visible light. Due to the very fast reduction of incident irradiation, such an optical element can be used as an optical safeguard device.

The processes which comprise a step of contacting the nanoparticles with a substance, e.g. a biological molecule, or with a carrier, in an advantageous manner do not have a previous step for removal of an organic compound from the suspension of the nanoparticles. Therefore, in processes according to the invention, nanoparticles can be arranged on carriers e.g. without chemical or thermal steps, especially without calcination, such that according to the invention the steps are not required which e.g. in case of a content of carbon in a nanoparticle preparation are necessary for removal of organic compounds.

$H_2O_2$ or ozone as inorganic oxidizing agent are advantageous in that they can be removed from water forming the medium by irradiation with light, by pressure reduction and/or an increase of temperature. Correspondingly, the process can optionally comprise the step of irradiating the medium having the nanoparticles contained therein in order to especially at least to a fraction remove the inorganic oxidizing agent consisting of $H_2O_2$ or ozone subsequent to irradiating the flow of the medium having the first particles suspended therein, wherein the medium contains the inorganic oxidizing agent. Preferably therein the medium is put under underpressure and/or is irradiated with irradiation of a wavelength at which the inorganic oxidizing agent is decomposed, e.g. in the UV-range, such that the inorganic oxidizing agent and its decomposition products can exit in a gaseous form.

The device is especially devised for performing the steps of the process.

DETAILED DESCRIPTION OF THE INVENTION

Figure 2:
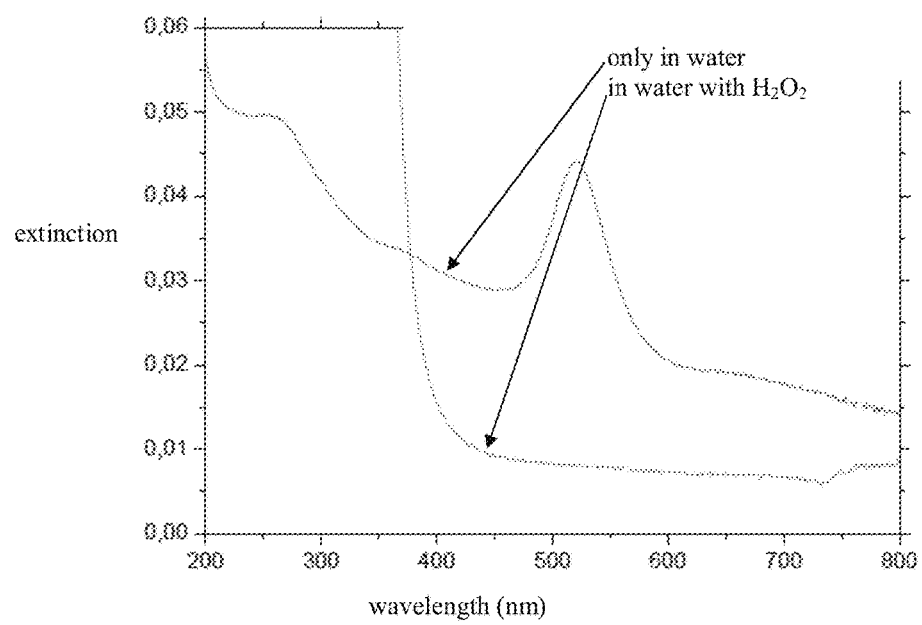
Figure 3A:
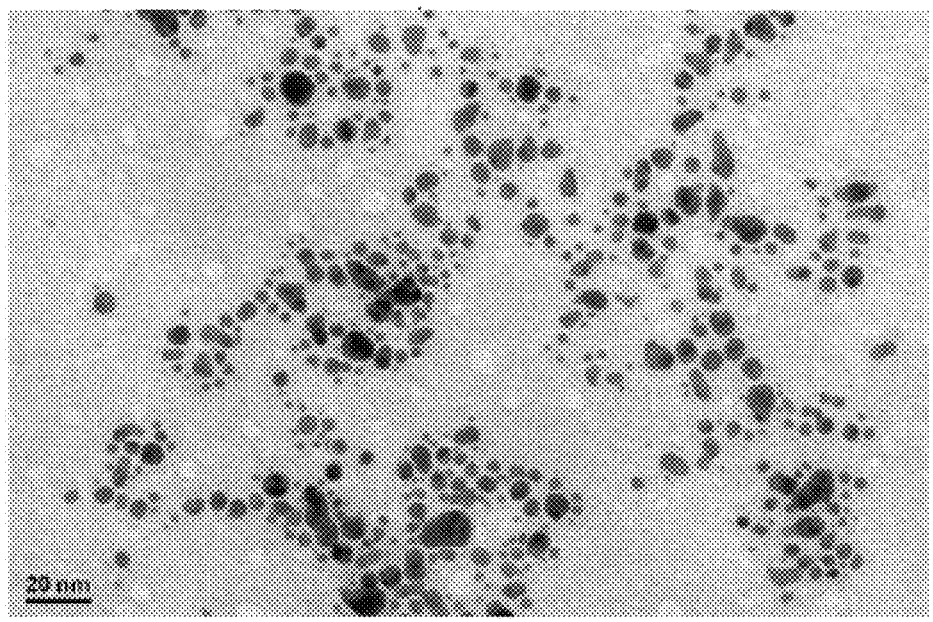
Figure 3B:
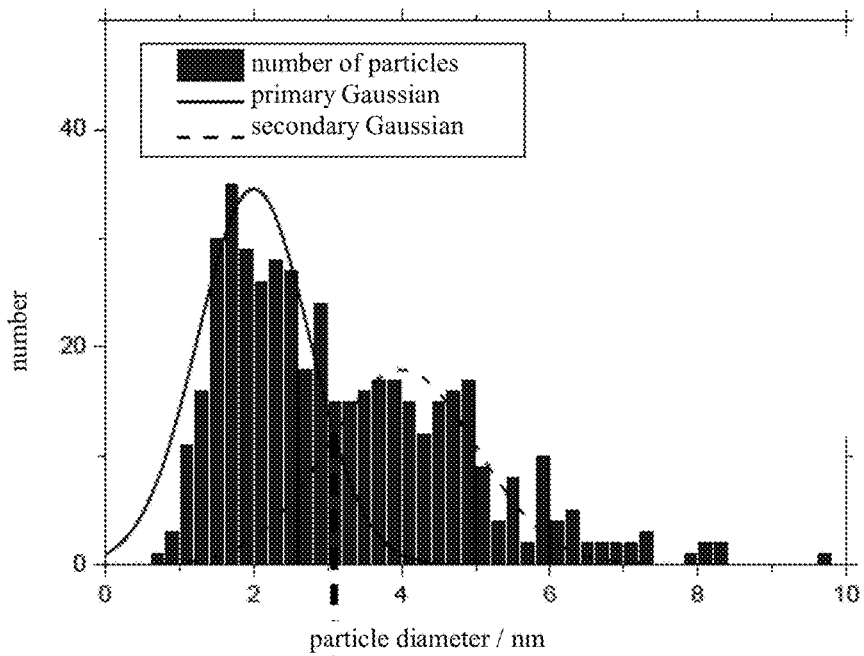
Figure 3C:
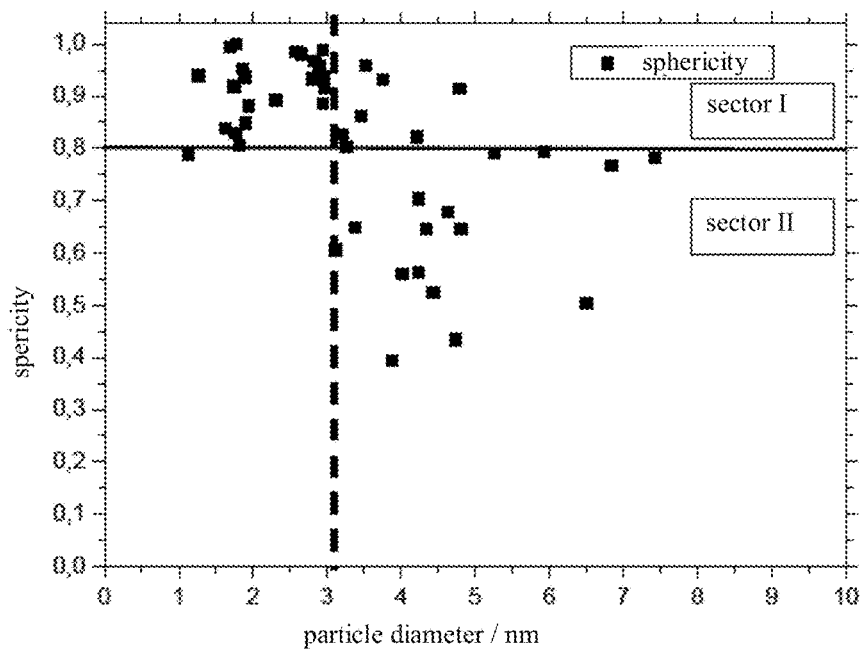
Figure 3D:
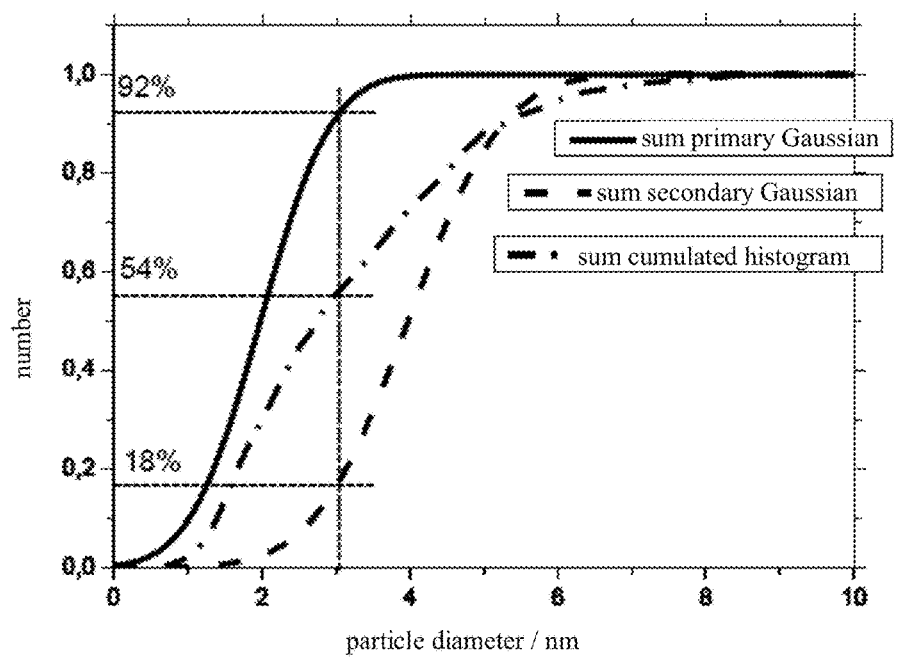
Figure 3E:
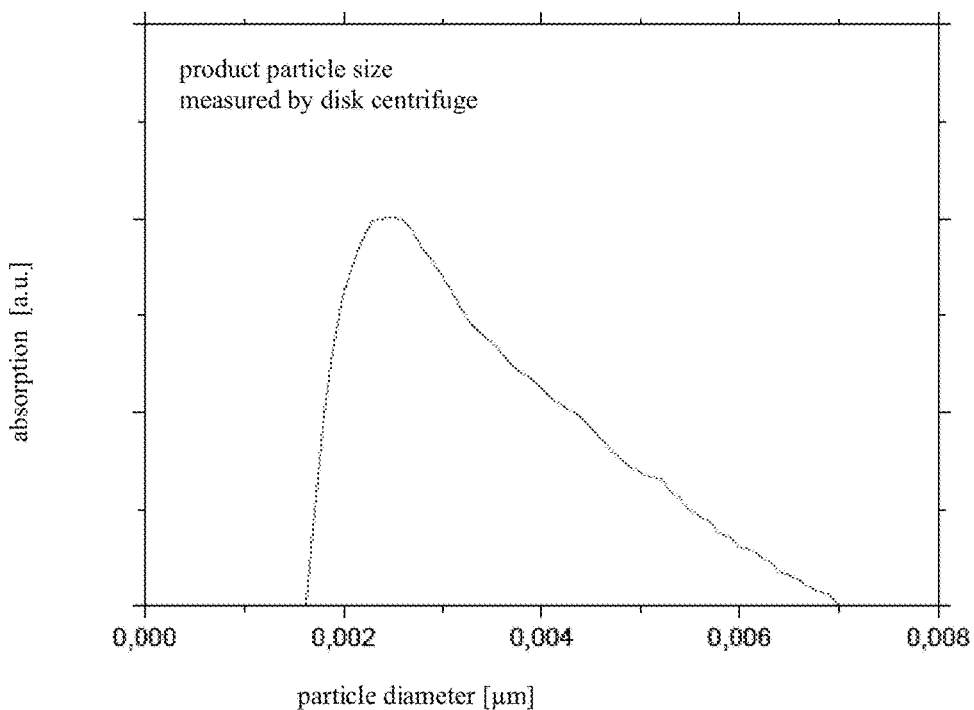
Figure 4:
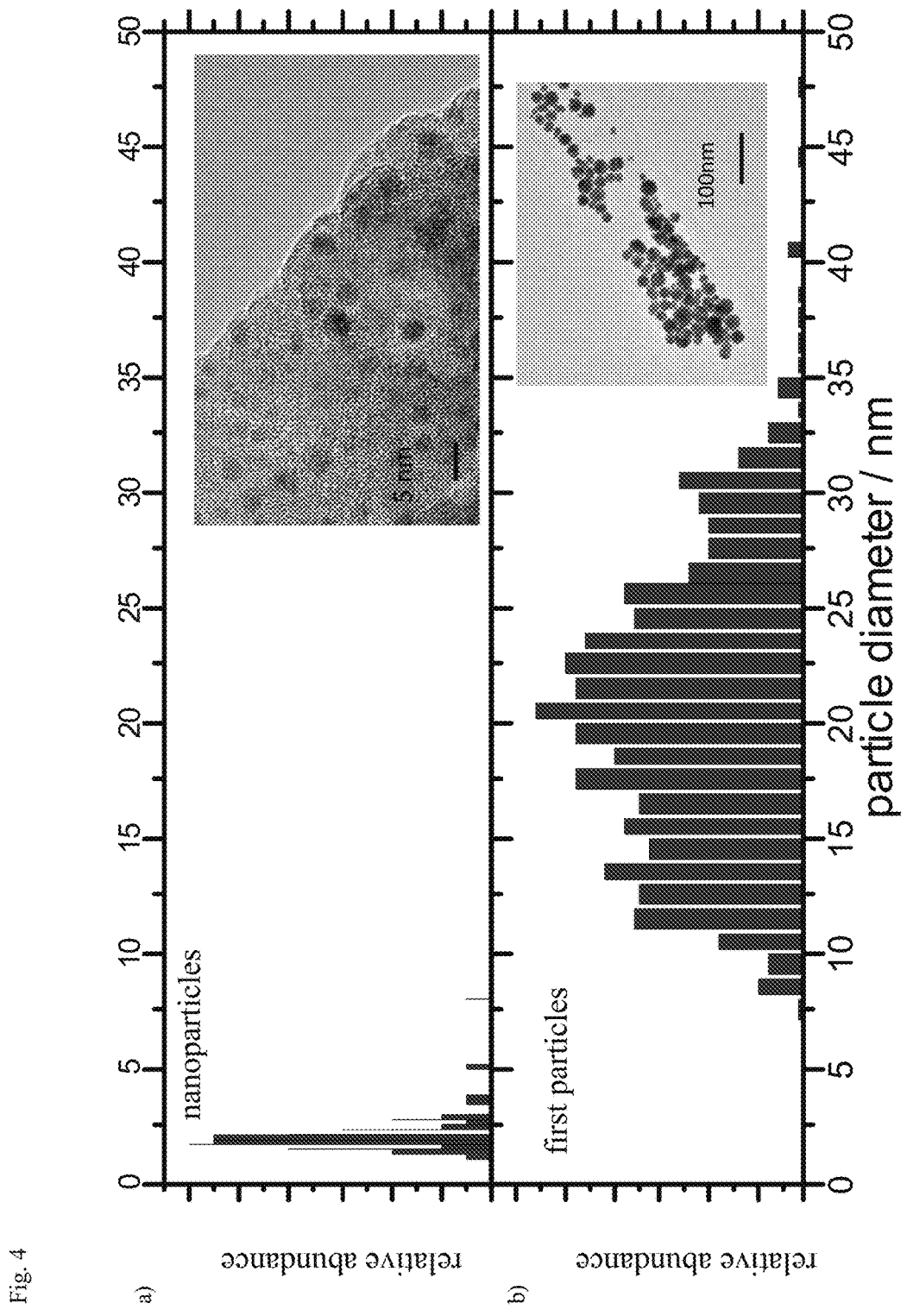
Figure 5:
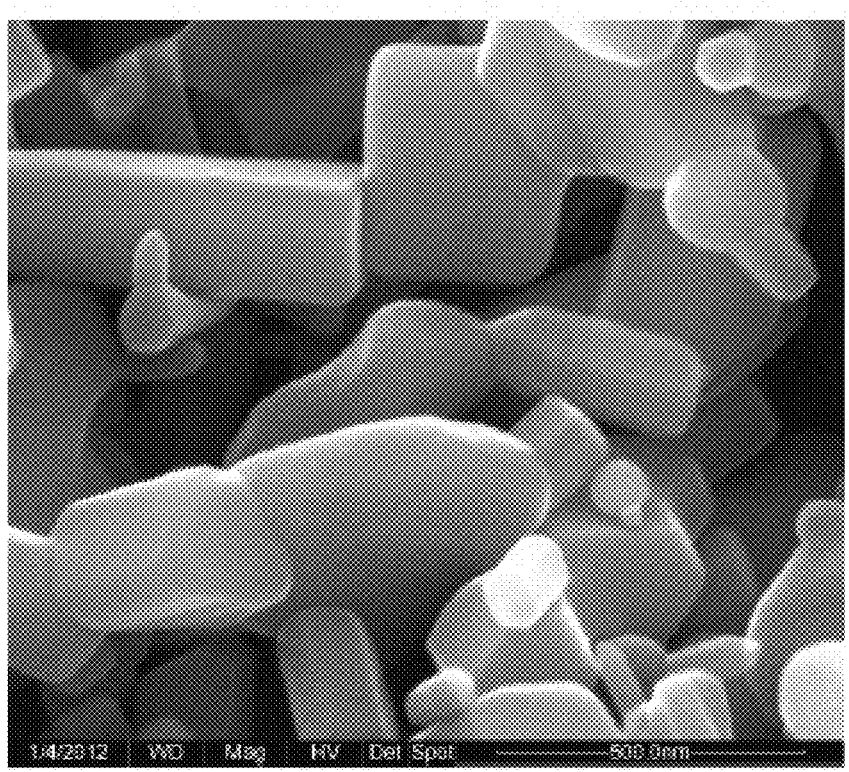
Figure 6:
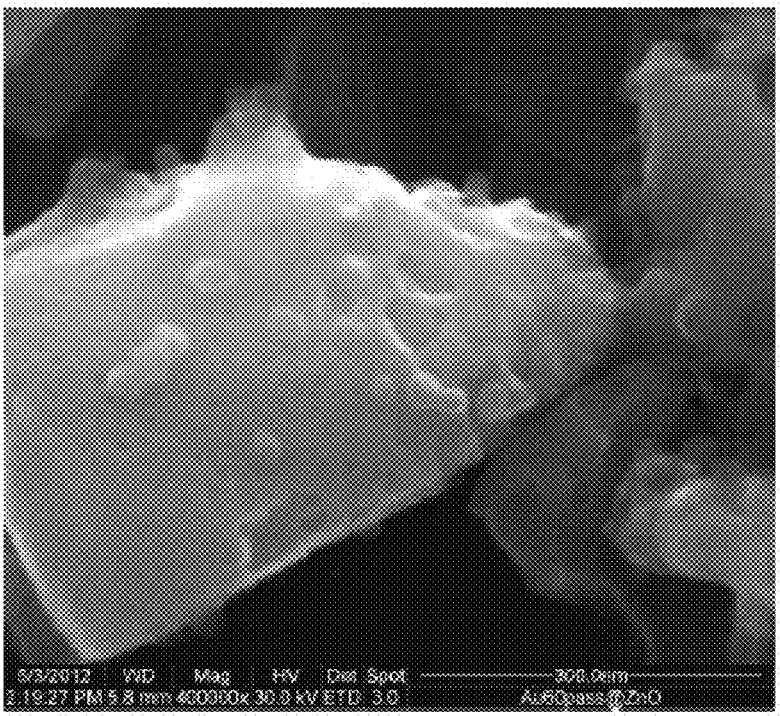
Figure 7:
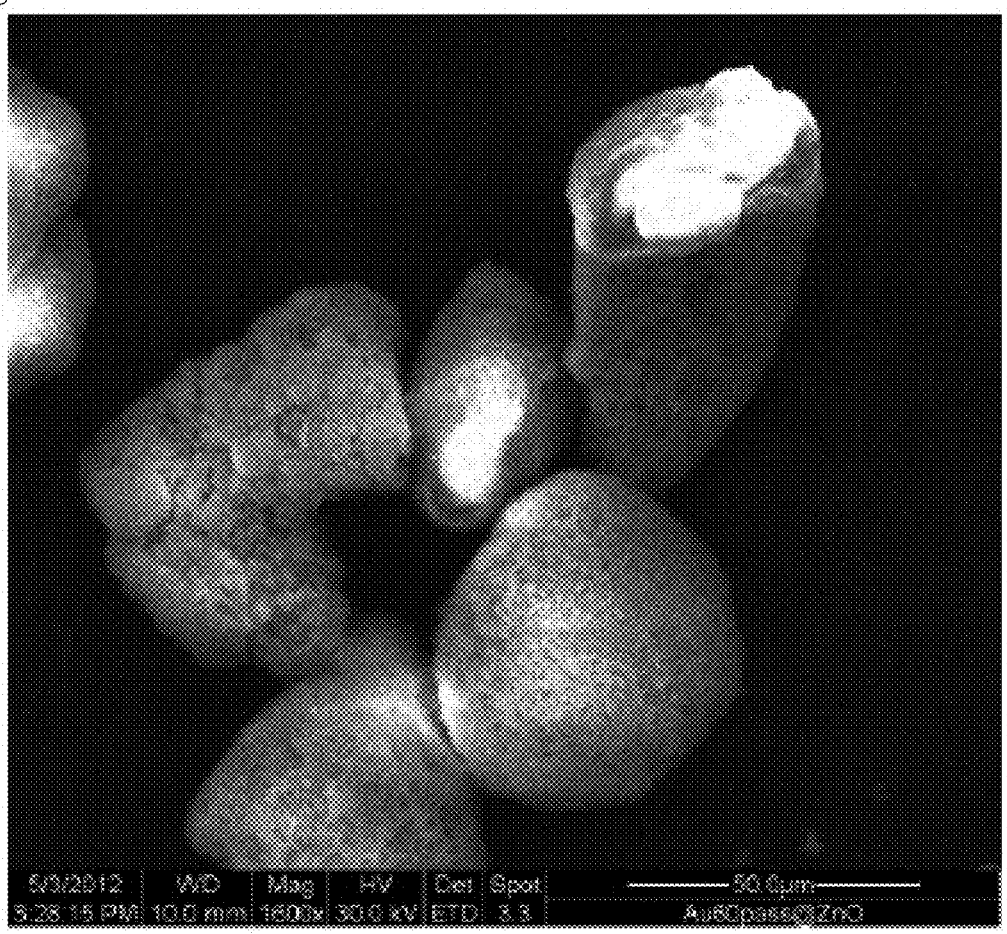
Figure 8:
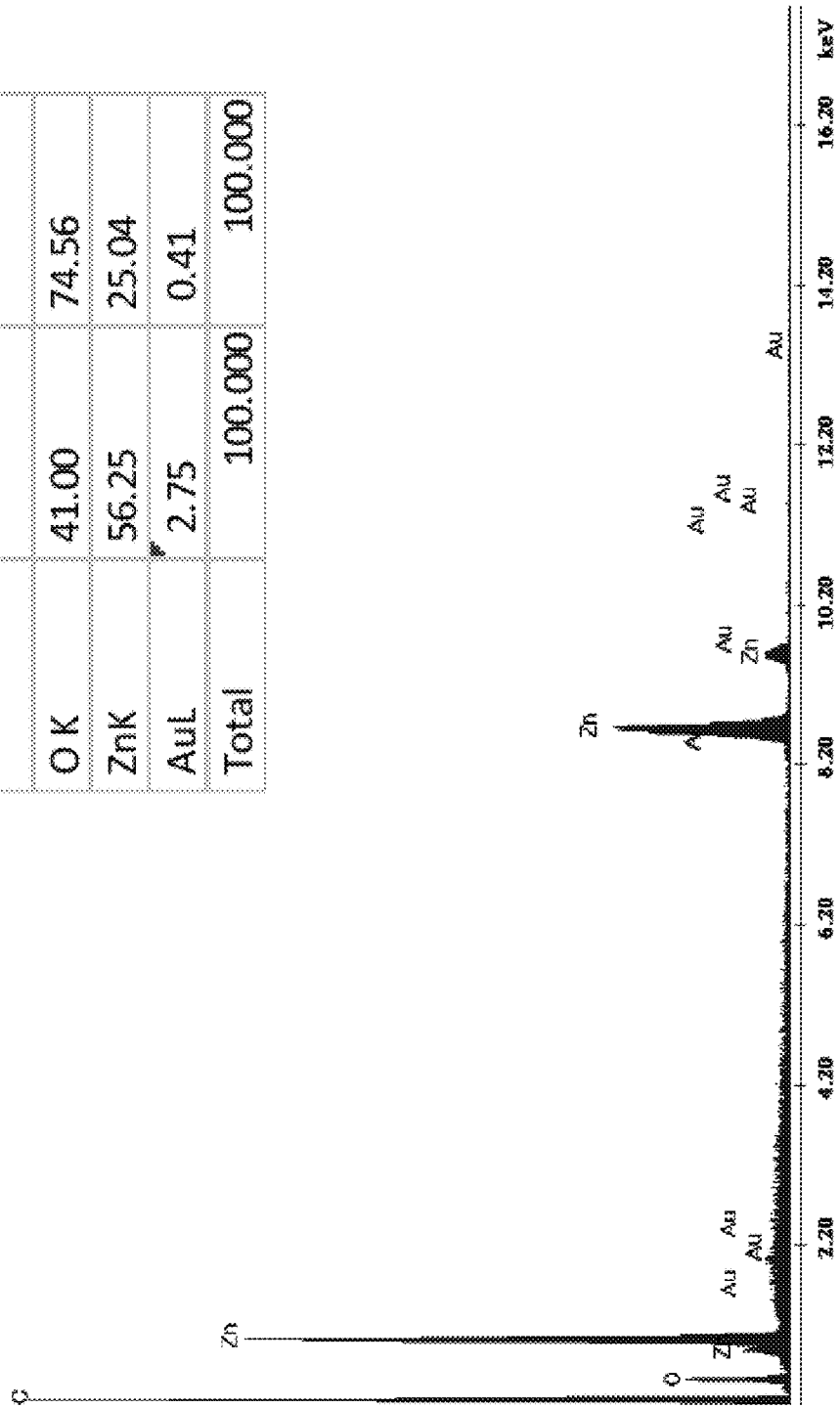
Figure 9A:
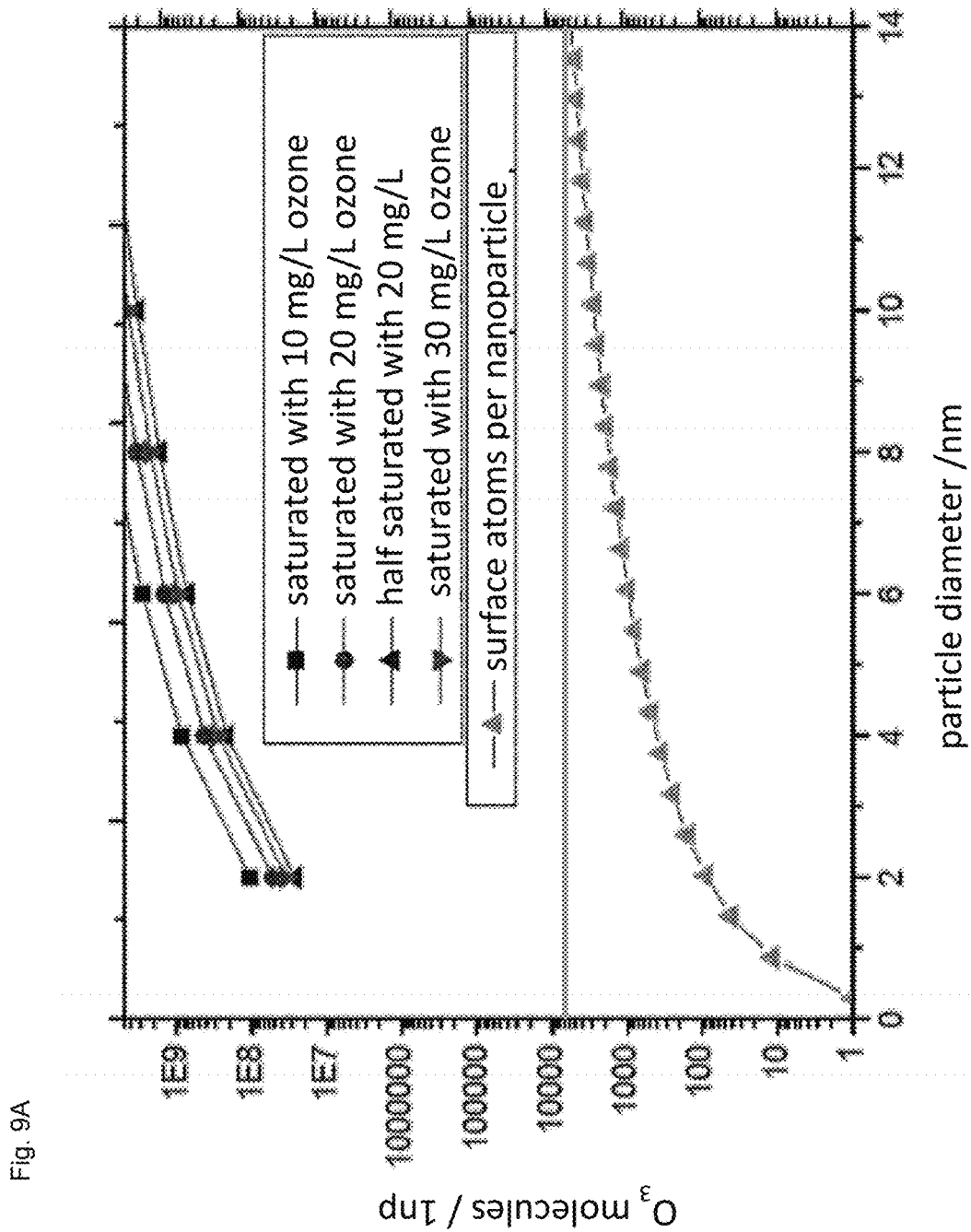
Figure 9B:
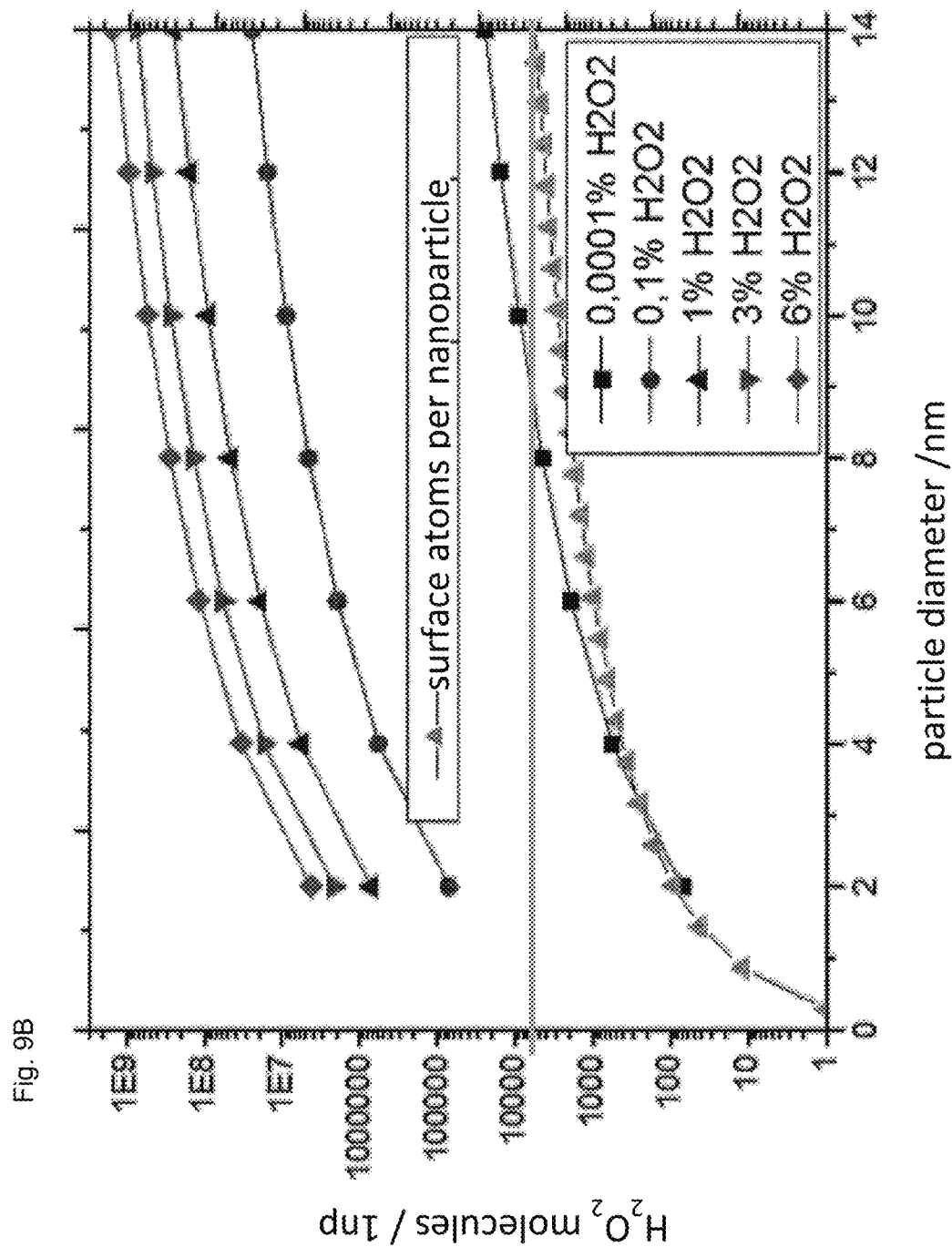
Figure 9C:
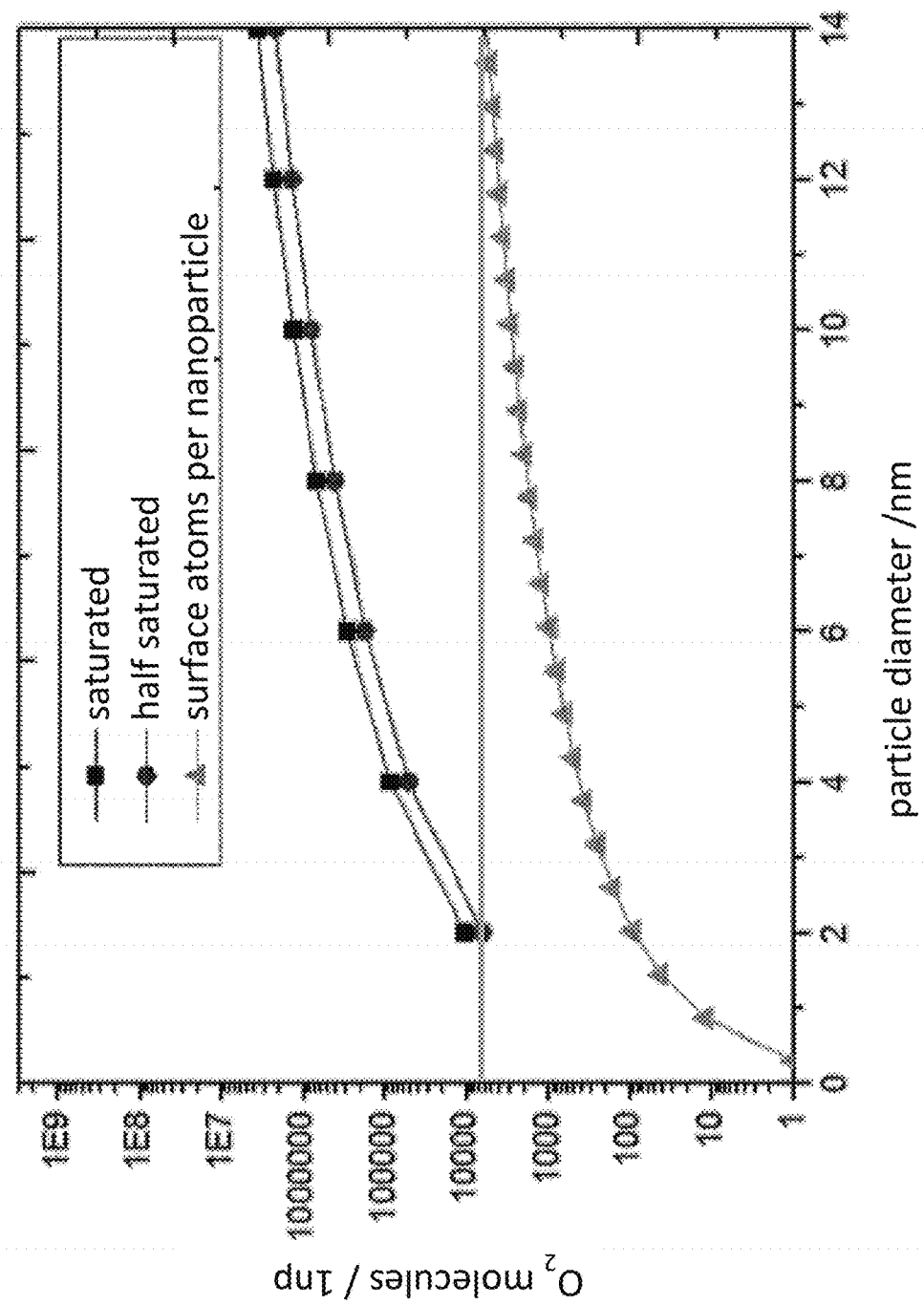

The invention is now described in greater detail by the way of examples and with reference to the figures which show in FIG. 1 schematically the arrangement of a device according to the invention, FIG. 2 a photospectrum of nanoparticles produced according to the invention in water with $H_2O_2$, FIG. 3a the TEM-photo of nanoparticles according to the invention, FIG. 3b the size distribution of nanoparticles produced according to the invention measured by way of TEM, FIG. 3c a graphic representation of the sphericity of nanoparticles according to the invention, FIG. 3d a graphic representation of the sum distribution of sizes of nanoparticles according to the invention, FIG. 3e a graphic representation of sizes of nanoparticles according to the invention, measured by means of a disk centrifuge, FIG. 4 in a) the relative abundance of sizes of nanoparticles produced according to the invention and their electron microscopic representation, and in b) the relative abundance of sizes of first particles and their electron microscopic representation, FIG. 5 a scanning electron microscopic photo of a carrier, FIG. 6 a scanning electron microscopic photo of a carrier with nanoparticles according to the invention arranged thereon, FIG. 7 a scanning electron microscopic photo of a carrier with nanoparticles according to the invention arranged thereon, FIG. 8 the result of an EDX-analysis of nanoparticles according to the invention on a carrier, and FIG. 9 the calculated molar concentration of oxidizing agents and the calculated number of surface atoms of nanoparticles of gold at a concentration of 20 mg/L.

EXAMPLE 1: PRODUCTION OF NANOPARTICLES OF GOLD

As the metal containing body, 99.99% gold arranged in highly purified water having a content of 10 wt.-% $H_2O_2$ was irradiated with laser pulses of 10 ns at a wavelength of 1064 nm having a maximum energy of 80 mJ per pulse, beam diameter 6 mm at a distance of approximately 100 mm from the lens (focus 100 mm) and the metal body at a pulse repetition rate of 100 Hz. The layer height of the medium between the metal body and the laser was approximately 1 cm, the pH value of the water ca. 3 to 5.

It could be observed that at the metal body a red coloring spread within the liquid, as is known for gold nanoparticles. A plasmon resonance (increased extinction) at 520 nm showed. These first particles agglomerated to hydrodynamic diameters of ca. 50 nm, measured by means of dynamic laser light scattering and measurements in a disk centrifuge.

The medium with the first nanoparticles produced in this way under the influence of gravity or by means of a pump exited through a nozzle which was arranged within a larger glass body as a protective container. The nozzle was directed vertically to the ground and the medium having the first particles suspended therein generated a free falling flow of ca. 1.2 mm diameter. A second laser, having the same beam properties as the previously utilized laser but a frequency-doubled wavelength of 532 nm was focused on the flow of the medium such that the focused laser completely covered the flow of the medium in one section. The speed of the flow was ca. 0.6 m/s and the volumemetric exchange rate of the irradiated section was 100 Hz. The nanoparticles obtained showed a size of smaller than approximately 5 nm, a median quantity size distribution of approximately 2.5 nm and generally showed no resonance frequency in the green range, especially none at 520 nm as is shown in the spectrum of FIG. 2. The red colouring and extinction at 520 nm of the first particles completely disappeared when the medium repeatedly passed through the second laser beam, e.g. up to 60 times. In a preferred embodiment the nanoparticles that were generated by irradiating the flow of the medium having the first particles suspended therein were irradiated at least once again in a free flow of medium by the second pulsed laser irradiation, for example by recirculation of the nanoparticles suspended in the medium through the nozzle, again with sectionwise irradiation of the flow by the second pulsed laser irradiation. As generally preferred, the repetition rate of the laser was adapted to the speed of the flow such that each volume element of the flow is subjected to a pulse of the laser irradiation exactly one time.

The nanoparticles obtained were stable as a suspension without further additive to the medium which contained inorganic oxidizing agent, e.g. for at least 4 d, preferably for at least 5 to 30 d. The stability could also be seen in that no plasmon resonance occurred, which is a sign for an agglomeration of non-plasmon resonant nanoparticles.

The device utilized for this process is schematically shown in FIG. 1. Therein, a container 1 contains the metal body 2 of gold in a holding device and is surrounded by medium 3. A first laser 4 generates the first laser irradiation 5, which is directed through an optically transparent window 6 of the container 1 onto the metal body 2. Preferably, container 1 is a chamber flowed through by medium 3, the chamber having an inlet and an outlet. Subsequent to the irradiation with first laser irradiation 5, the medium 3 is transported, optionally continuously, from container 1 to a reservoir. Optionally, a spectrometer 20 is arranged in the duct between the container 1 and the reservoir 7 and/or in the duct between the reservoir 7 and the nozzle 8, which spectrometer 20 is devised for measuring the extinction. By way of this arrangement, the spectrometer 20 is arranged in a duct which is arranged upstream to the nozzle 8 and is therefore disposed to measure the medium fed to the nozzle 8. Preferably, a spectrometer 20 is arranged to control the dosing device for addition of the inorganic oxidizing agent. The medium 3 having the first particles contained therein is fed from the reservoir 7 to a nozzle 8, which is directed vertically to the ground and generates a free medium flow 9. For avoiding the formation of aerosols, the nozzle 8 is arranged within a housing 10 in which the medium flow 9 freely falls, optionally driven by a pump. A section of the flow of the medium 9 is irradiated by the second laser irradiation 12 generated by a second laser 11, the second laser irradiation 12 e.g. passing through a window or whole 13 of the housing 10 that is transparent for the second laser irradiation 12. As indicated schematically the window 13 can have or consist of an optical element, especially a collimating lens. The housing 10 has an outlet 14 out of which the medium exits that now contains the nanoparticles therein, for example into a collecting vessel 15. Optionally, at the outlet 14 there is arranged a further spectrometer 21, which can especially be connected with a control device of the second laser 11 or with a control device of the pump that drives the medium flow 9. The collecting vessel 15 can be connected to the nozzle 8 by means of a return duct in order to allow for a repeated irradiation of the medium now having the nanoparticles contained therein and/or first particles with second laser irradiation 12. A carrier 18 can be arranged in the collecting vessel 15, wherein the carrier 18 especially covers the cross-section of the flow of the collecting vessel 18. Such a carrier is e. g. arranged in the collecting vessel 15 in order to arrange nanoparticles on the carrier 18. The carrier 18 can e.g. be titanium dioxide or aluminium oxide as a powder or moulding, onto which nanoparticles sorb. In the return duct 16, which can have a pump, optionally a filter 19 is arranged that retains particles having a size above a preset size, e.g. retaining particles having a size above 10 nm. A dosing device for inorganic oxidizing agent is shown by way of a reservoir 17 for the oxidizing agent which is connected by means of a duct to the duct that leads to the nozzle 8. In this way the dosing device, which preferably is controlled in dependence on the spectrometer 21 arranged at the outlet 14, can be devised to introduce inorganic oxidizing agent into the medium containing first particles.

FIG. 2 shows a spectrum of nanoparticles of gold produced according to the invention in water containing $H_2O_2$ in comparison to nanoparticles of gold in pure water, and therefore without inorganic oxidizing agent, which were otherwise produced by the same process. The absence of the plasmon resonance at 420 nm of nanoparticles according to the invention shows that the nanoparticles produced according to the invention in the medium having a content of an inorganic oxidizing agent are smaller than 5 nm, especially smaller than 3.5 nm in diameter and did not aggregate to one another to larger plasmon resonant aggregates. The particles according to the invention also subsequent to storage for e.g. 20 d show the same optical properties and therefore prove the stability of the nanoparticles which are suspended in the medium. As a reason for this stability there is presently assumed an electrostatic stabilization of the nanoparticles. Therefore the suspension of nanoparticles which is obtainable by the process according to the invention can also be termed an electrostatically stabilized colloid.

FIG. 3a shows the particle sizes of nanoparticles of gold produced according to the invention in a TEM-photo which are deposited on a grid and measured in a transmission electron microscope (TEM). These data show that the nanoparticles produced according to the invention have a mean particle size of ca. 3 nm and a size range of ca. 1-5 nm.

FIG. 3b shows the size distribution of nanoparticles according to the invention which were determined from TEM-photos. In the size distribution, a primary and a secondary Gaussian distribution were determined. The particle size that lies in the intersection of the Gaussian distributions is shown as the border on the representation of the sphericity in FIG. 3c. For a sphericity of below 0.8 (sector II) no spherical form is assumed.

From FIGS. 3b and 3c it results that the spherical form particles in sector I are nanoparticles according to the invention having a particle size of smaller than 5 nm, wherein their main portion has a size of smaller than 3 nm.

From the data of FIGS. 3b and 3c one can conclude that larger particles possibly are first particles or were formed as artifacts during the preparation of the particles on the TEM-grid, e.g. caused by removal of the inorganic oxidizing agent.

FIG. 3d shows the sum distribution of single and cumulated Gaussian distributions. It can be seen from this that preferably 92% of all particles generated by the process are present in the medium with a diameter of smaller than 3 nm.

The data of the measurement of the sizes of nanoparticles by means of a disk centrifuge are shown in FIG. 3e. These data confirm that nanoparticles produced according to the invention essentially have a size of smaller than 5 nm with a mean size of smaller than 3 to smaller than 4 nm.

FIG. 4a shows the size distribution of these nanoparticles produced according to the invention and an inset electron microscope picture of these nanoparticles. FIG. 4b shows the size distribution of the first particles generated by means of laser irradiation to the gold body arranged in water having 10% wt.-% $H_2O_2$. The electron microscopical picture inset in FIG. 4b shows these first particles. In the alternative, the water in this step can be without additive. The first particles show a diameter of ca. 7.5 to maximally 50 nm, especially of ca. 10 to 35 nm having a mean particle size of 20, e.g. for at least 90% of first particles.

These results show that the nanoparticles produced according to the invention have a size of essentially below 5 nm, preferably of 1 to 3 nm, e.g. having a mean size of 2.5 nm, generally preferred with a mono-modal size distribution.

EXAMPLE 2: PRODUCTION OF A COMPOUND OF NANOPARTICLES WITH ORGANIC LIGANDS

Nanoparticles of gold produced according to Example 1 in a medium having a content of $H_2O_2$ where first transferred to a non-oxidizing medium. Subsequently, the suspension of the nanoparticles was contacted with an organic ligand as an example for a substance, for example with an oligonucleotide, a protein, preferably a binding molecule, especially an antibody, or with a polysaccharide. Optionally, the substance contained a thiol group.

It has shown that the nanoparticles obtainable according to the invention have a sufficient reactivity for forming a bond with the organic molecule added as the substance. The organic molecules therefore were labelled by the nanoparticles. The compounds obtained of the substance with nanoparticles produced according to the invention where fluorescent and not plasmon resonant, as is generally preferred.

EXAMPLE 3: COATING OF AN INORGANIC CARRIER WITH NANOPARTICLES

As an example for an inorganic carrier, zinc oxide or an electrode having a metal surface was used. The nanoparticles were deposited on the carrier by contacting with the medium containing the nanoparticles. Therein it showed that no external or additional electrical field was necessary for arranging the nanoparticles on the carrier. The nanoparticles could alternatively be deposited on the surface of the carrier by electrophoretic deposition and formed an adsorbing layer on the carrier that preferably had superficial charges. The zinc oxide that was coated by the nanoparticles of gold was characterized by a homogenous arrangement or layer, respectively, of sorbed nanoparticles. FIG. 5 shows the zinc oxide particles used as a carrier in a scanning electron microscope (REM) picture, FIGS. 6 and 7 show the zinc oxide particles following contacting with the suspended nanoparticles. Here it becomes clear that these nanoparticles sorb onto the surface of the carrier.

FIG. 8 shows an EDX-analysis of nanoparticles of gold according to the invention, which are arranged on a ZnO-carrier. Oxygen was determined by means of the K-line (O K), zinc by means of the K-line (ZnK) and gold by means of the L-line (AuL) of the spectrum.

From the EDX-analysis it becomes clear that the nanoparticles of gold which are non-plasmon resonant and which preferably are clusters, are sorbed on the carrier and form a non-plasmon resonant coating.

FIG. 9 shows the calculated molar concentrations of oxidizing agents ozone, $H_2O_2$ (according to the invention) and oxygen, each at standard pressure under standard conditions in water (not according to the invention), as well as those for a gold nanoparticle size of 2 nm at a concentration of 20 mg/L calculated molar concentration of nanoparticles. It shows that for $H_2O_2$ a concentration of 1 wt.-% already gives a molar relation higher by a factor of 1000 to the molar concentration of nanoparticles than the saturation with oxygen.

On the example of gold nanoparticles the number of surface atoms of nanoparticles is given for the given particle sizes. This makes it clear that with increasing size of the nanoparticles the number of surface atoms of each nanoparticle increases, but not in a linear way.

EXAMPLE 4: PRODUCTION OF AN OPTICAL ELEMENT

As an example for an optical element a glass was contacted with the nanoparticles suspended in the medium. The medium could have the content of inorganic oxidizing agent, alternatively, the inorganic oxidizing agent could be removed from the medium.

The nanoparticles obtainable according to the invention could be deposited on the glass by mere contacting with the suspension.

The optical element produced this way under irradiation, especially at a wavelength range of 350 to 1064 nm showed a limitable non-transparency which shows the suitability of the nanoparticles obtainable according to the invention for use as optical limiters against radiation of this wavelength.

EXAMPLE 5: PRODUCTION OF NANOPARTICLES OF GOLD

In accordance with Example 1, first particles were irradiated with pulsed laser irradiation, wherein the first particles were not generated by irradiation of the metal body with first laser irradiation, but were synthesized by colloid chemistry and were present in aqueous medium. These first particles had PVA for stabilization.

For removal of the organic carbon compound PVA prior to irradiation with pulsed laser irradiation the medium, in which the first particles were contained was washed at least 3-fold with ultra pure water and resuspended in ultra pure water, admixed with $H_2O_2$ in additional quantity stochiometrically sufficient for complete oxidation of organic carbon compounds and/or were irradiated additionally with a pulsed laser prior to adding $H_2O_2$.

The irradiation of the first particles was preferably performed in a free liquid flow, in the alternative in a container under stirring.

The invention claimed is:
1. Process for the production of nanoparticles of gold and/or a metal of the platinum group, comprising: providing first particles of gold and/or of the platinum metal suspended in an aqueous medium, adding an inorganic oxidizing agent to the aqueous medium, wherein the inorganic oxidizing agent has a redox potential in the aqueous medium higher than that of an oxidized form of the first particles of gold and higher than that of an oxidized form of the first particles of the platinum metal, and irradiating the medium having the first particles suspended therein with a pulsed laser irradiation, whereby a suspension of the nanoparticles in the medium is generated, and wherein the aqueous medium is free from organic carbon compounds other than $CO_2$.

2. Process according to claim 1, wherein the first particles have a size of at maximum 200 nm.

3. Process according to claim 1, wherein the providing the first particles comprises removal or oxidation of organic compounds from an admixture of the organic compounds and the first particles.

4. Process according to claim 1, wherein the providing comprises generation of a flow of the aqueous medium to which the inorganic oxidizing agent is added and having the first particles suspended therein, and wherein the irradiating comprises directing pulsed laser irradiation is directed onto at least a section of the flow.

5. Process according to claim 4, wherein the flow of the medium having the first particles suspended therein is a free liquid flow.

6. Process for the production of nanoparticles of gold and/or a metal of the platinum group, comprising: providing first particles of gold and/or of the platinum metal suspended in an aqueous medium, adding an inorganic oxidizing agent to the aqueous medium, wherein the inorganic oxidizing agent has a redox potential in the aqueous medium higher than that of an oxidized form of gold and/or higher than that of an oxidized form of the metal of the platinum group, and irradiating the medium having the first particles suspended therein with a pulsed laser irradiation, whereby a suspension of the nanoparticles in the medium is generated, wherein the providing comprises generation of a flow of the aqueous medium to which the inorganic oxidizing agent is added and having the first particles suspended therein, and wherein the irradiating comprises directing pulsed laser irradiation is directed onto at least a section of the flow, and wherein the diameter of the section of the flow is at maximum as large as the focus of the pulsed laser irradiation directed onto this section.

7. Process according to claim 1, wherein the first particles suspended in the aqueous medium are provided by production by application of a first pulsed laser irradiation onto a metal containing body containing gold and/or a metal of the platinum group arranged in an aqueous medium, or by wire erosion of a metal containing body in the form of a wire of gold and/or of a metal of the platinum group in the aqueous medium, wherein the aqueous medium is free from organic carbon compounds.

8. Process according to claim 1, wherein the pulsed laser irradiation has a wavelength of 330 to 1500 nm at a repetition rate of at least 10 Hz.

9. Process according to claim 1, wherein the medium in which the first particles are suspended consists of water with an inorganic oxidizing agent contained therein and the oxidizing agent is selected from the group consisting of $H_2O_2$, dissolved ozone, a derivative of oxygen—hydrogen compounds, a nitrogen oxide, antimonic acid, arsenious acid, arsenic acid, boric acid, chlorous acid, bromous acid, chloric acid, chromic acid, cyanic acid, dichromic acid, disulphuric acid, hypochlorous acid, hypobromous acid, hypoiodous acid, iodous acid, iodic acid, isocyanic acid, carbonic acid, metasilicilic acid, molybdic acid, orthodisilicilic acid, orthosilicilic acid, perbromic acid, perchloric acid, periodic acid (orthoperiodic acid), peroxodisulphuric acid, peroxonitric acid, nitric acid, nitrous acid, sulphuric acid, sulphurous acid, telluric acid, thiosulphuric acid, tungstic acid and its salts, hypofluorous acid, hypofluorite, oxyacid of chlorine, hypochlorite, chlorite, chlorate, perchlorate, oxyacid of bromine, hypobromite, bromous acid, bromite, bromic acid, bromate, perbromic acid, perbromate, oxyacids of iodine, hypoiodite, iodite, iodic acid, iodate, orthoperiodic acid, periodate, meta-periodic acid and admixtures of these, wherein the inorganic oxidizing agent comprises a gas dissolved in the aqueous medium, wherein the inorganic oxidizing agent has a redox potential in the aqueous medium that is higher than that of the oxidized form of gold and/or the oxidized form of the metal of the platinum group by at least an amount of an overpotential of the gas compared to the nanoparticles.

10. Process according to claim 1, wherein the nanoparticles suspended in the medium are subsequently contacted with a substance which is selected from organic ligands, an inorganic carrier and an optically active solid.

11. Process according to claim 1, wherein the pulsed laser irradiation has a fluence of the least 0.8 $J/cm^2$.

12. Process according to claim 1, wherein the nanoparticles are clusters.

13. Process according to claim 1, wherein the aqueous medium carbon-free.

14. Process according to claim 1, wherein the aqueous medium consists of water and the inorganic oxidizing agent with or without $CO_2$.

15. Process according to claim 10, further comprising removing the inorganic oxidizing agent prior to the nanoparticles suspended in the medium being contacted with the substance.

16. Process for the production of nanoparticles of a metal of the platinum group, comprising: providing first particles of the metal of the platinum group suspended in an aqueous medium, adding an inorganic oxidizing agent to the aqueous medium, wherein the inorganic oxidizing agent has a redox potential in the aqueous medium higher than that of an oxidized form of the metal of the platinum group, and irradiating the medium having the first particles suspended therein with a pulsed laser irradiation, whereby a suspension of the nanoparticles in the medium is generated, and wherein the aqueous medium is free from organic carbon compounds other than $CO_2$.

17. Process according to claim 16, wherein the first particles have a size of at maximum 200 nm.

18. Process according to claim 16, wherein the providing the first particles comprises removal or oxidation of organic compounds from an admixture of the organic compounds and the first particles.

19. Process according to claim 18, wherein the diameter of the section of the flow is at maximum as large as the focus of the pulsed laser irradiation directed onto this section.

20. Process according to claim 16, wherein the providing comprises generation of a flow of the aqueous medium to which the inorganic oxidizing agent is added and having the first particles suspended therein, and wherein the irradiating comprises directing pulsed laser irradiation is directed onto at least a section of the flow.

21. Process according to claim 20, wherein the flow of the medium having the first particles suspended therein is a free liquid flow.

22. Process according to claim 16, wherein the first particles suspended in the aqueous medium are provided by production by application of a first pulsed laser irradiation onto a metal containing body containing a metal of the platinum group, or by wire erosion of a metal containing body in the form of a wire of a metal of the platinum group, wherein the aqueous medium is free from organic carbon compounds.

23. Process according to claim 22, wherein the metal containing body is a pure metal or a metal alloy of at least two metals of the platinum group.

24. Process according to claim 16, wherein the pulsed laser irradiation has a wavelength of 330 to 1500 nm at a repetition rate of at least 10 Hz.

25. Process according to claim 16, wherein the pulsed laser irradiation has a fluence of the least 0.8 J/cm$^2$.

26. Process according to claim 25, wherein the medium in which the first particles are suspended consists of water with an inorganic oxidizing agent contained therein and the oxidizing agent is selected from the group consisting of $H_2O_2$, dissolved ozone, a derivative of oxygen—hydrogen compounds, a nitrogen oxide, antimonic acid, arsenious acid, arsenic acid, boric acid, chlorous acid, bromous acid, chloric acid, chromic acid, cyanic acid, dichromic acid, disulphuric acid, hypochlorous acid, hypobromous acid, hypoiodous acid, iodous acid, iodic acid, isocyanic acid, carbonic acid, metasilicilic acid, molybdic acid, orthodisilicilic acid, orthosilicilic acid, perbromic acid, perchloric acid, periodic acid (orthoperiodic acid), peroxodisulphuric acid, peroxonitric acid, nitric acid, nitrous acid, sulphuric acid, sulphurous acid, telluric acid, thiosulphuric acid, tungstic acid and its salts, hypofluorous acid, hypofluorite, oxyacid of chlorine, hypochlorite, chlorite, chlorate, perchlorate, oxyacid of bromine, hypobromite, bromous acid, bromite, bromic acid, bromate, perbromic acid, perbromate, oxyacids of iodine, hypoiodite, iodite, iodic acid, iodate, orthoperiodic acid, periodate, meta-periodic acid and admixtures of these, wherein the inorganic oxidizing agent comprises a gas dissolved in the aqueous medium, wherein the inorganic oxidizing agent has a redox potential in the aqueous medium that is higher than the oxidized form of the metal of the platinum group by at least an amount of an overpotential of the gas compared to the nanoparticles.

27. Process according to claim 16, wherein the nanoparticles suspended in the medium are subsequently, optionally following removal of the inorganic oxidizing agent, contacted with a substance which is selected from organic ligands, an inorganic carrier and an optically active solid.

28. Process according to claim 16, wherein the nanoparticles are clusters.

29. Process according to claim 16, wherein the aqueous medium carbon-free.

30. Process according to claim 1, wherein the aqueous medium consists of water and the inorganic oxidizing agent with or without $CO_2$.

* * * * *